US00PP21842P2

(12) United States Plant Patent
Hurd

(10) Patent No.: US PP21,842 P2
(45) Date of Patent: Apr. 5, 2011

(54) ***DIANTHUS* PLANT NAMED 'APPLE SLICE'**

(50) Latin Name: ***Dianthus* hybrid**
Varietal Denomination: Apple Slice

(75) Inventor: Kevin A. Hurd, Zeeland, MI (US)
(73) Assignee: Walters Gardens Inc., Zeeland, MI (US)

( * ) Notice: Subject to any disclaimer, the term of this patent is extended or adjusted under 35 U.S.C. 154(b) by 9 days.

(21) Appl. No.: 12/462,743

(22) Filed: Aug. 7, 2009

(51) Int. Cl.
*A01H 5/00* (2006.01)

(52) U.S. Cl. ..... Plt./272
(58) Field of Classification Search ..... Plt./272
See application file for complete search history.

*Primary Examiner* — Annette H Para

(57) ABSTRACT

The new and distinct cultivar of perennial Carnation or Pinks, *Dianthus* plant named 'Apple Slice' with long-blooming, fragrant, highly double flowers and petals with a central rose pink zone surrounded on the outside and usually bisected down the middle with a magenta border. *Dianthus* 'Apple Slice' is tolerant of high temperatures and resists center dying out.

2 Drawing Sheets

Botanical denomination: *Dianthus* hybrid.
Cultivar designation: 'Apple Slice'.

BACKGROUND OF THE INVENTION

The present invention relates to the new and distinct cultivar of *Dianthus* or Pinks from the genus *Dianthus* and assigned the cultivar name 'Apple Slice'. The new plant was the result of an intentional cross in May of 2006 by Kevin A. Hurd between 'Double Spotty' U.S. Plant Pat. No. 13,884 as the seed parent and 'Devon Siskin' U.S. Plant Pat. No. 14,377 (more often known as 'Raspberry Swirl') as the pollen parent. The new hybrid was first isolated from trials at a nursery in Zeeland, MI during the summer of 2007. *Dianthus* 'Apple Slice' has been asexually propagated at the same nursery in Zeeland, MI using traditional shoot tip cutting procedures and found to reproduce plants that are identical and exhibit all the characteristics of the original plant.

SUMMARY OF THE INVENTION

The present invention has not been evaluated under all possible environmental conditions. The phenotype may vary with variations in environment including: growing temperature, available sunlight, nutrients, water, etc. without a change in the genotype of the plant. The new plant is distinct from its parents and all other *Dianthus* known to the applicant in the following combined traits:

1. Double flowers with high petal counts.
2. Unique floral color pattern.
3. High heat tolerance.
4. Floriferous habit.
5. Vigorous growth and excellent habit.
6. Compact, distinctly blue-green foliage.

BRIEF DESCRIPTION OF THE DRAWINGS

The photographs of the new invention demonstrate the overall appearance of the plant including the unique traits. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
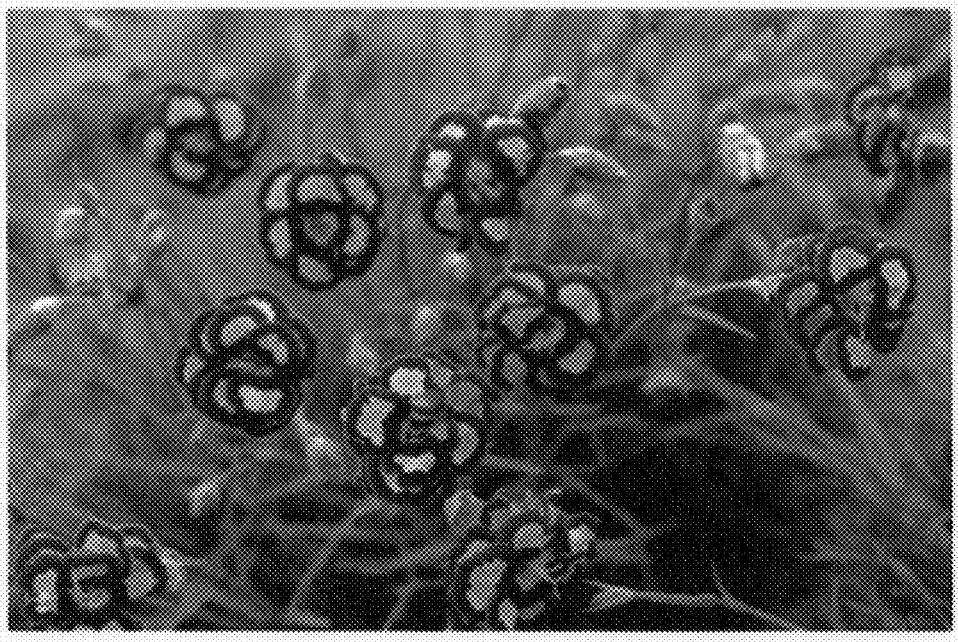
FIG. 1 shows the new plant in flower.
Figure 2:
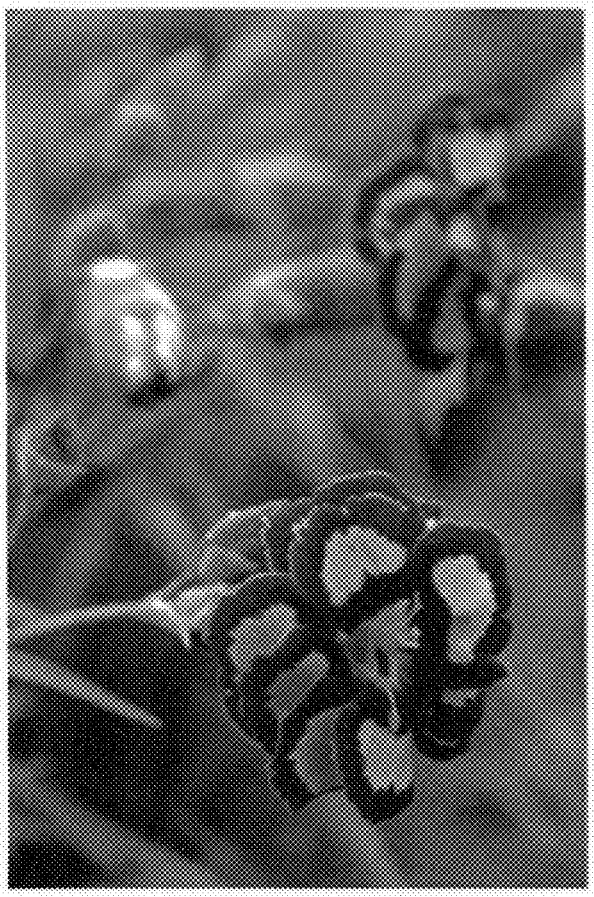
FIG. 2 shows a close-up of the flower and bud.
Figure 3:
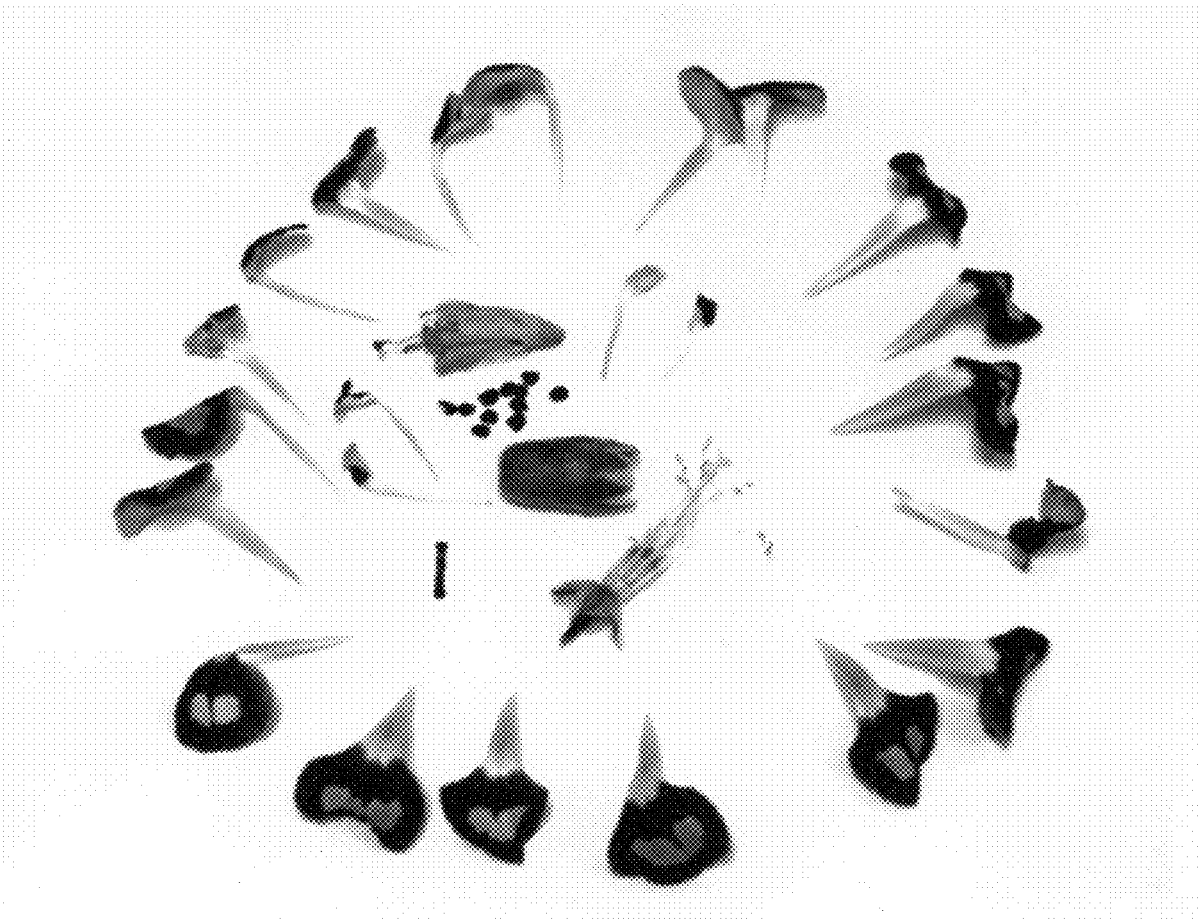
FIG. 3 shows the dissected flower of the new plant together with capsule and seeds.

The following detailed description of the new plant is based on observations of two-year old plants in open-field, full-sun conditions in Zeeland, MI with supplemental watering, light additions of fertilizer and free of other plant growth regulators. All color usage is in reference to the 2001 edition of The Royal Horticultural Colour Chart except where common dictionary terms are used.

Botanical classification: *Dianthus* hybrid.

Parentage: 'Double Spotty' (female) times 'Raspberry Swirl' (male).

Plant description:

*Habit.*—Cespitose, herbaceous, evergreen perennial; stems proximally branched, erect; height of foliage about 14 cm and 35 cm across.

*Root system.*—Fibrous; Venation: finely reticulate, coloration same as that of leaf top and bottom.

Foliage:

*Leaf type.*—Simple, linear, opposite, decussate, sessile, glabrous, glaucous on adaxial and abaxial; acute apex; base decurrent, adpressed along stem and somewhat perfoliate; no fragrance detected.

*Leaf dimensions.*—About 7 cm long and 4 mm wide.

*Leaf color.*—Nearest RHS 122B adaxial and abaxial sides.

*Venation.*—Finely reticulate, coloration same as that of leaf top and bottom.

*Stems.*—Erect to arching, terete, glabrous, glaucous, proximally branching at 2 to 3 nodes.

*Stem size.*—About 22 cm long and 3 mm wide at base.

*Stem color.*—Nearest RHS 122B.

*Branching.*—Numerous from lower leaf axils; about 120 per plant.

*Nodes.*—4 mm across, RHS N134A.

*Internodes.*—4 to 5 cm apart.

Inflorescence:

*Type.*—Terminal, cymose, erect.

*Flowers per stem.*—Usually 4 to 6.

*Pedicel.*—Glaucous, glabrous, terete.

*Pedicel size.*—Usually 3 to 4 cm long and 2 mm diameter.

*Pedicel color.*—Nearest RHS 122A.

Flowers:

*Type.*—Salviform, completely double, symmetrical.

*Dimension.*—4.0 to 4.5 cm across and extending about 1.5 cm above calyx.

*Flower bud shape.*—Rhomboid to terete.

*Flower bud size one day prior to opening.*—About 2 cm long and 1 cm wide.

*Flower bud color.*—Glaucous, nearest RHS N138B and with patches between RHS 187B and RHS N187B.

*Flower period.*—Starting early June and after a 2 week rest continuing until frost.

*Flower lasting quality.*—about one week on or off the plant.

*Flower fragrance.*—Light, sweet spicy, clove-like.

*Petals.*—20 to 24, consisting of a rounded blade or limb and a claw (enclosed completely within the calyx), obovate, apex dentate with dentations 2 mm deep, bearded with minute hairs mostly on the center of the adaxial surface, bent outwardly to nearly a ninety degree angle; dark wine-colored margin circle on adaxial side about 5 mm thick; variable center stripe either continuous to 2 mm wide, broken or not present.

*Dimension.*—Variable, to 3.8 cm long including claw and limb; larger petal limb to 2.3 cm across and 1.5 cm long, smaller limbs to 3 mm across and 6 mm long; claws range from 1.7 cm to 2.5 cm long and 2 mm to 8 mm wide about 3 mm from limb.

*Color.*—Adaxial limb: margin circle or center stripe RHS N77A to N79A, middle portion RHS 71D; abaxial limb: margin or center stripe (showing through from adaxial side) closest to RHS N187C and the center portion between RHS 63C and RHS 63D; claw: RHS 145C both sides.

*Calyx.*—Glabrous, glaucous, five-toothed corolla tube fused in proximal 1.5 cm; about 2 cm long and 0.8 cm in diameter; RHS 147D with anthocyanin tinting of RHS N77C.

*Peduncle.*—Glabrous, glaucous, terete, 22 cm long and 2 mm diameter; RHS N138D.

*Bracts.*—Two, opposite, broadly obtuse with rounded apex, about 7 mm long and 10 mm wide; RHS N138C in the center, lighter than RHS 138D at base and margins.

*Bracteoles.*—Two, opposite, lanceolate, sharply acute apex, bases joined at stem; about 10 mm long and 4 mm wide; glaucous, RHS N138C at apex and center, lighter than RHS 138D at base and margins.

*Stipules.*—None present.

*Androecium.*—Stamens 10, filaments variable in length from 1.2 to 3 cm long, less than 1 mm diameter; pale green lighter than RHS 11D; anther oblong to 3.2 mm long and 1 mm wide, RHS164B; pollen rare, pollen color RHS 11D.

*Gynoecium.*—Style split in two above ovary, pistil 2 cm long and about 1 mm diameter, lighter than RHS 11D except for distal 5 mm which are lighter than RHS 77D; stigma between RHS 77C and RHS 77B.

*Ovary.*—Superior, ovoid; 1.1 cm long and 8 mm wide; RHS 135B at distal end and between RHS 145D and RHS 145C at proximal end.

Seed: 12 to 30, blackish brown darker than RHS 200A, shield-shaped, dorsiventrally compressed, about 3.0 mm across and 0.5 mm thick.

Capsule: Ovoid to cylindrical, opening by 4 teeth, about 2 cm long and 7.5 mm diameter, between RHS 197B and RHS 197C.

Growth rate.—Vigorous, finishing from a 3 cm liner into a 15 cm in 6 to 8 weeks.

Disease resistance: The new plant is resistant to center die out from fungus or high temperatures. The plant grows best with adequate moisture and well-drained soil, but is able to tolerate high temperatures and some drought once established. Hardiness at least from USDA zone 4 through 9.

Comparison varieties: The new plant has more petals, with wider and deeper ruby petal margins, and deeper pink petal centers than either parent. The most closely known cultivars are *Dianthus* 'Cranberry Ice' U.S. Plant Pat. No. 18,342 which is similar in petal color but has only a single row of petals and copending application *Dianthus* plant named 'Coconut Punch' which has much lighter (whiter and less pink) adaxial petal limb centers and abaxial petal limb sections.

I claim:

1. A new and distinct cultivar of perennial Carnation or Pinks, *Dianthus* plant named 'Apple Slice' as herein described and illustrated, with fragrant highly double flowers, petals with a central rose pink zone surrounded on the outside and usually bisected down the middle with a magenta border, tolerant of high temperatures, resistant to center die out and suitable as a garden ornamental, potted plant and for cut flower arrangements.

* * * * *